US010639012B2

(12) United States Patent
Elvira Segura et al.

(10) Patent No.: US 10,639,012 B2
(45) Date of Patent: May 5, 2020

(54) METHOD FOR DETECTING CIRCULATING CELLS IN SUPERFICIAL BODY FLUIDS (71) Applicants: CONSEJO SUPERIOR DE INVESTIGACIONES CIENTIFICAS, Madrid (ES); FUNDACION PARA EL CONOCIMIENTO MADRI+D, Madrid (ES); MASSACHUSETTS INSTITUTE OF TECHNOLOGY, Cambridge, MA (US)

(72) Inventors: Luis Elvira Segura, Madrid (ES); Oscar Martinez Graullera, Madrid (ES); Shiva Kant Shukla, Madrid (ES); Francisco Montero, Madrid (ES); Javier Jimenez, Cambridge, MA (US); Ian Richard Butterworth, Cambridge, MA (US); Brian Anthony, Cambridge, MA (US); John Lee Haeseon, Cambridge, MA (US); Carlos Castro Gonzalez, Cambridge, MA (US)

(73) Assignees: CONSEJO SUPERIOR DE INVESTIGACIONES CIENTIFICAS (CSIC), Madrid (ES); FUNDACION PARA EL CONOCIMIENTO MADRI+D, Madrid (ES); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 253 days.

(21) Appl. No.: 15/760,453

(22) PCT Filed: Sep. 19, 2016

(86) PCT No.: PCT/EP2016/072125
§ 371 (c)(1),
(2) Date: Mar. 15, 2018

(87) PCT Pub. No.: WO2017/046412
PCT Pub. Date: Mar. 23, 2017

(65) Prior Publication Data
US 2018/0263602 A1 Sep. 20, 2018

Related U.S. Application Data (60) Provisional application No. 62/219,802, filed on Sep. 17, 2015.

(51) Int. Cl.
*A61B 8/00* (2006.01)
*A61B 8/08* (2006.01)
(Continued)

(52) U.S. Cl.
CPC .............. *A61B 8/5223* (2013.01); *A61B 8/58* (2013.01); *G01N 15/02* (2013.01);
(Continued)

(58) Field of Classification Search
CPC .............. G01N 15/02; G01N 15/0211; G01N 15/1056; G01N 29/02; G01N 29/032;
(Continued)

(56) References Cited

U.S. PATENT DOCUMENTS 6,029,507 A 2/2000 Faber et al.
8,208,995 B2 * 6/2012 Tearney ............... A61B 5/0062
600/476

(Continued)

FOREIGN PATENT DOCUMENTS

RU 2093833 C1 10/1997
RU 2189782 C1 9/2002
(Continued)

OTHER PUBLICATIONS

Moon et al.; "Integrating microfluidics and lensless imaging for point-of-care testing"; Biosensors and Bioelectronics; Jul. 2009; pp. 3208-3214; vol. 24 Issue 11; Elsevier.
(Continued)

Primary Examiner — David J Bolduc
(74) Attorney, Agent, or Firm — Hayes Soloway PC (57) ABSTRACT

The present invention relates to a method for measuring circulating cells in superficial body fluids by means of high-frequency-based device. The method can be used for detecting circulating cells in the fluids of an individual without the necessity of extracting a sample of the individual, being useful as a diagnostic tool and for monitoring the effectiveness of a treatment administered to an individual suffering from a viral, protozoal, fungal and/or bacterial disease.

20 Claims, 6 Drawing Sheets

(51) Int. Cl.

| | | |
|---|---|---|
| *G01N 15/10* | (2006.01) | |
| *G01N 29/02* | (2006.01) | |
| *G01N 15/02* | (2006.01) | |
| *G01N 29/032* | (2006.01) | |
| *G01N 15/06* | (2006.01) | |

(52) U.S. Cl.
CPC ..... *G01N 15/0211* (2013.01); *G01N 15/1056* (2013.01); *G01N 29/02* (2013.01); *G01N 29/032* (2013.01); *A61B 8/0891* (2013.01); *G01N 2015/0687* (2013.01); *G01N 2015/1006* (2013.01); *G01N 2015/1075* (2013.01); *G01N 2015/1087* (2013.01); *G01N 2291/02466* (2013.01)

(58) Field of Classification Search
CPC ... G01N 2015/0687; G01N 2015/1006; G01N 2015/1075; G01N 2015/1087; G01N 2291/02366; A61B 8/5223; A61B 8/58; A61B 8/0891
See application file for complete search history.

(56) References Cited

U.S. PATENT DOCUMENTS

| | | | |
|---|---|---|---|
| 2004/0054283 A1 | 3/2004 | Corey et al. | |
| 2004/0059220 A1* | 3/2004 | Mourad | A61B 5/0048 600/442 |
| 2004/0122319 A1 | 6/2004 | Mehi et al. | |
| 2008/0154128 A1* | 6/2008 | Milner | A61B 5/0066 600/427 |
| 2012/0020542 A1 | 1/2012 | Tafas et al. | |
| 2013/0237826 A1 | 9/2013 | Levien | |
| 2013/0269416 A1* | 10/2013 | Myrick | A61M 1/32 73/19.03 |
| 2014/0187963 A1* | 7/2014 | Corl | A61B 8/54 600/467 |
| 2014/0349326 A1 | 11/2014 | Ingber | |
| 2015/0025380 A1* | 1/2015 | Azegami | A61B 8/085 600/438 |
| 2015/0094582 A1* | 4/2015 | Tanaka | A61B 8/06 600/441 |
| 2016/0192867 A1* | 7/2016 | Esenaliev | A61B 5/0095 600/316 |
| 2016/0238568 A1* | 8/2016 | Feleppa | A61B 8/08 |
| 2018/0014810 A1* | 1/2018 | Chen | A61B 8/06 |
| 2018/0153520 A1* | 6/2018 | Esenaliev | G16H 40/63 |

FOREIGN PATENT DOCUMENTS

| | | |
|---|---|---|
| WO | 2006055449 A2 | 5/2006 |
| WO | 2009052481 A1 | 4/2009 |

OTHER PUBLICATIONS

Sheehusen et al., "Cerebrospinal Fluid Analysis", Tripler Army Medical Center, Honolulu, Hawaii, Research Gate, https://www.researchgate.net/publication/9068277, American Family Physician, Oct. 2003, 7 pages.

Kaplan, MD, "Clinical features and diagnosis of acute bacterial meningitis in children older than one month of age", UpToDate 19.3, Dec. 7, 2018, 21 pages.

* cited by examiner

FIG. 10

# METHOD FOR DETECTING CIRCULATING CELLS IN SUPERFICIAL BODY FLUIDS

The present invention relates to a method for measuring circulating cells in superficial body fluids by means of high-frequency-based device. The method can be used for detecting circulating cells in the fluids of an individual without the necessity of extracting a sample of the individual, being useful as a diagnostic tool and for monitoring the effectiveness of a treatment administered to an individual suffering from a viral, protozoal, fungal and/or bacterial disease. In particular, this method is useful for the diagnosis of meningeal infection and/or inflammation through the detection of circulating cells in the cerebrospinal fluid.

BACKGROUND ART

The patent application RU2093833 refers to a method to predict pathological changes in brain and spinal cord of infants and young children through a neurosonography. In order to obtain said neurosonography at least an ultrasound sensor is placed in a defected bone in the spine or in the fontanelle of an infant. This sensor operates at one of the following frequencies of 3.5, 5.0, 7.5 MHz. In particular, the method described by RU2093833 comprises scanning the cerebrospinal fluid and determining the protein level. When the protein level increases, the viscosity of the cerebrospinal fluid varies. Due to this fluid variation, the protein level in the cerebrospinal fluid can be detected. When the protein content in the CSF is higher than 0.8 g/L, it indicates a pathological change as meningitis or encephalitis. The method is based on density/viscosity changes of the CSF due to increased protein levels as an indication of infection or inflammation; this is a low sensitive cerebrospinal fluid (CSF) parameter to meningitis. Additionally, this method requires of some invasive procedures to the body to obtain an accurate measurement.

The patent application RU2189782 discloses a method for predicting development of bacterial purulent meningitis in children of early age. In particular this method analyses the parameters of neurosonographic images of patients taken during the first week of the disease. These images are taken in the fissure between the hemispheres, in order to obtain the echogenicity and echogenic structure of the brain for predicting neurologic injuries. The method predicts purulent meningitis by means of assessing structural changes that occur in the disease at a later stage. Thus, the present method does not allow an early meningeal infection diagnosis when the CSF is not yet purulent, and an accurate CSF cellulality change neither, which is the parameter most used to track patient's response to treatment.

The international patent application WO2006055449 refers to a system and a method for ultrasonic measuring of the properties of a variety of particles or cells in a suspension. Those properties are, for example, velocity of particles, concentration and/or size. In order to measure these properties an acoustic energy is introduced to a focal zone and a narrow band interrogating signals is used. The acoustic energy may cause movement or streaming of the fluid or suspension. The acoustic streaming may allow a Doppler effect measurement, without any other source, of velocity. This patent application also describes the use of ultrasonic backscatter to characterize concentration, particle size, and viscosity of the suspension. Also this ultrasonic backscatter time-domain signals may be converted by a Fast Fourier Transform ("FFT") algorithm to a high-resolution, narrow-band power spectrum, the shape of which provides the information about the particle suspension. The patent claims a method directing an ultrasonic single frequency tone burst of at least 10 cycles. Such long signals reduce the ability of the system to resolve individual cells subjecting concentration measurements to normalization/characterization of the backscattered signal to a background or reference signal. This normalization is impractical in vivo for each patient because the different attenuation of the skin in each patient made a previous reference, obtained in vitro or from other patients, invalid.

The international patent application WO2009052481 discloses an optical coherence tomography cell detection system. In particular, the objective of this invention is imaging blood flow using magneto-motive optical Doppler tomography (MMODT), Optical Coherence Tomography (OCT), or Ultrasound. At least one of these methods is directed into the body of the patient and red blood cells, which are suspended in the blood plasma, scatter the ultrasonic energy back towards a receiver/transducer that converts the backscattered ultrasonic energy into an electrical signal that is processed in some known manner to determine the presence of a flow and an estimate of the flow velocity. However, this method requires high-concentration of red blood cells to be sensitive to backscatter signal shifts. With such high concentration of cells, ultrasound frequencies in the range of 5-10 MHz are generally needed.

Accordingly, it would be desirable to have methods and processes that do not suffer from one or more of the above drawbacks.

DETAILED DESCRIPTION OF THE INVENTION

The key to achieve an early diagnosis of some diseases is the detection of individual cells to get an in vivo efficient measurement of cell concentration at low concentration ranges (1-1,000 cells/µL). As shown in the examples, the method disclosed herewith provides a solution for the above-mentioned drawbacks, by means of detecting cells at very low concentrations using high frequency ultrasound and short-duration acoustic pulse trains.

Thus, in one aspect, the present invention relates to a non-invasive method for detecting and quantifying circulating cells in superficial body fluids, hereinafter first method of the invention, comprising
a) placing an ultrasound-based device on the skin of the subject for obtaining a ultrasound data of the superficial body fluid under the skin;
b) analyzing the ultrasound data obtained in step a) by a data processing system which provides information about cells and their concentration in the fluid, and
c) correlating the information obtained in step b) with the presence and the amount of circulating cells in the individual,
wherein the ultrasound-based device operates at a central frequency in the range of 10-50 MHz, and at a pulse duration between 50-1,000 ns, and at wavelengths between 30 and 150 µm.

In the context of the present invention, the term "non-invasive" refers to a process where the skin in the individual is not broken for extracting a sample. Thus, the first method of the invention further to be non-invasive is painless at the same time, i.e., it is a process which does not cause physical pain.

The first method of the invention is useful for detecting circulating cells in superficial body fluids. Any cell which runs through a fluid in the human body is considered a "circulating cell" and can be detected by the present method. In a particular embodiment, the circulating cells are white blood cells, red blood cells or cancer cells.

The term "superficial body fluids" refers to fluids of the human body which flow close enough to the skin so that they are reached by high frequency ultrasound waves in the range mentioned (10-50 MHz). This may comprise body fluids not deeper than 50 mm, preferably, 20 mm. In a particular embodiment, the superficial body fluid is selected from the group consisting of cerebrospinal fluid (CSF), blood, urine, pleural fluid, synovial fluid and pericardial fluid.

The present method is especially useful for measuring circulating cells in infants within the cerebrospinal fluid without the necessity of performing a lumbar puncture. As the skilled person in the art knows, the fontanelles are soft spots on a baby's head which, during birth, enable the bony plates of the skull to flex, allowing the child's head to pass through the birth canal. The ossification of the bones of the skull causes the anterior fontanelle to close over by 9 to 24 months. Thus, before the fontanelle is closed, the CSF that surrounds the brain is accessible, allowing the physician to measure the circulating cells using the method of the invention, whose concentration can be indicative of an infection or inflammation in the central nervous system, such as meningitis or encephalitis.

Further advantage of the first method of the invention is that not only the circulating cells of the superficial fluids are detected or measure, but other properties of the cell can also be assessed, such as size, variability, concentration, etc., as well as properties of the fluid, such as viscosity which can provide information on protein concentration in the fluid, and being indicative of a disease.

The first step of the first method of the invention, step a), comprises placing an ultrasound-based device on the skin of the subject for obtaining an ultrasound data of the fluid under the skin.

Any ultrasound-based device can be used for putting into practice the present invention. Non-limiting examples of devices include a portable dermatology ultrasound device (system, probe and laptop) from Taberna Pro-Medicum (DUBSkinscanner 33 or 33 MHz), a pre-clinical imaging system from VisualSonics (Vevo 2100 and the transducer for the Vevo 770) (U.S. Pat. No. 7,255,678) and an ophthalmic probe from ArcScan (patent application US2013237826).

In a particular embodiment, the ultrasound-based device of the method of the invention comprises a transducer. As the skilled person in the art understands, a transducer is a device that converts one form of energy to another form of energy, i.e. ultrasound transducers convert variations of a physical quantity, such as pressure, into an electrical signal or vice versa.

Gel is usually placed between the transducer and the skin for a better acoustic impedance matching between the transducer and the skin, reducing thus signal loss during transmission and reception of the signal. The focal point of the ultrasound to obtain an optimal signal needs to be within the target region. Commonly, this focal point may be between 1-30 mm, preferably 20 mm, from the probe surface.

The transducer may comprise a single focused element, for example, a resonant flat piezoelectric ceramic crystal and concave focusing lens. Other transducers, for example, transducers with shaped piezoelectric elements to create focusing may be used. The resonances, while not very sharp, to obtain short pulses, may be used to maximize the transmitted signals and the reception sensitivities. Transducers may have different diameters (typically between 4-10 mm) and focal lengths (typically, between 5-15 mm). Any other suitable transducers with any diameters and focal lengths may be used. A single transducer in acoustic contact with the skin may to both launch the interrogating signal and receive the backscattered signals.

A set of transducers or an array may be also used. Signal focalization may be obtained in this case by using geometrically focalized elements, electronic focalization (by setting a proper delay for the emission of each transducer), synthetic focalization (by postprocessing the signals obtained) or a combination of some or all of them. Any other type of transducer that may generate an adequately large ultrasonic pressure signal in the fluid may be used.

In a particular embodiment, the signal emitted by the ultrasound-based device, or the transducer, operates at a central frequency of 20 MHz, and at a pulse duration of 500 ns, and at a wavelength of 75 µm.

Once the acoustic pulse is emitted by the transducer through the skin, reflected signals, or ultrasound data, from the tissue layer interfaces as well as from cells in the fluid are received and recorded by the transducer (we also refer to these signals as interface signals and scatters).

Next, the transducer receives an ultrasound data which is processed in step b). In a particular embodiment, the ultrasound data obtained in step a) is in the form of (i) collection of A-line data and/or of (ii) B-mode or C-mode type of 2D data or 3D data. A-line data refers to ultrasonic data obtained in one dimension and keeping the transducer position fixed; B-mode and C-mode refers to 2D or 3D data representations obtained as a function of the angle and transducer position (in moving systems) respectively. 2D and 3D data can be obtained either by moving a single-element transducer, or by using fixed or moving transducer arrays (linear or 2D arrays).

In a second step, step b), the first method of the invention comprises analyzing the ultrasound data obtained in step a) by a data processing system which provides information about cells and/or fluid properties.

In the present invention, a "data processing system" means the combination of electronics and algorithms to analyze the ultrasound data and provide cell type and concentration information as well as fluid bulk properties of the cells such as density or viscosity. In a particular embodiment, the data processing system comprises an algorithm.

In the context of the present invention, the terms "analyzing", "processing", "computing", "calculating", "determining", "deriving" and the like are equivalents and refer to the action and/or processes of a processor, computer or computer system, or similar electronic or hardware computing device, that manipulate and/or transform data represented as physical, such as electronic quantities within the computer system's register and/or memories into other data similarly represented as physical quantities within the computer system's memories, register or other information storage, transmission or display services.

The processes and displays presented herein are not inherently related to any particular computer, measurement device, electronic device or other apparatus. The desired structure for a variety of these systems will appear from the description below. In addition, embodiments of the present invention are not described with reference to any particular programming language, machine code, etc. It will be appreciated that a variety of programming languages, mathematical tools, electronic measurements tools, machine codes, etc. may be used to implement the teachings of the invention as described herein. Embodiments of the invention may be included in a medium or article such as a hard disc, CD, DVD, "disc on key", memory stick, or other memory unit having stored thereon instruction that when executed implement an embodiment of the invention, or having files or data corresponding to effects stored thereon.

Waves emitted by the transducers are backscattered from objects that have an acoustic impedance contrast with the medium in which they are suspended. This acoustic contrast may be due, for example, to a difference in the density or the compressibility of the particles from that of the fluid, or both. These differences may give rise to a difference between the acoustic impedances—the product of the particle or fluid density and sound wave speed, which is inversely proportional to the square root of the product of the density and the compressibility. The signals backscattered by these objects depend on the relative acoustic impedances of fluid and objects, the size and even the shape of these objects.

In the long wavelength limit where the wavelength of the acoustical energy being scattered may be greater than the size of a weakly scattering (nonresonant) particle, i.e., $\lambda > 2\pi a$ where $\lambda$ may represent the wavelength and "a" may represent the particle radius, the backscattered energy may be due to Rayleigh scattering and it may depend on the contrast between the compressibility and density of the particle and that of the fluid suspension medium, and the volume of the particle. For example, at the ultrasonic frequency of 20 MHz, the acoustic wavelength is 75 μm. For cells or other particles on the order of 10 μm or smaller the ratio $2\pi a/\lambda$ may be small (<1, with $a/\lambda < 1/10$) and the backscattering effect is within the Rayleigh regime. At higher frequencies and/or for larger particles, the backscattered power may become a function of other particle properties which may complicate interpretation of the amplitude of backscatter data.

The method of the invention may for example allow concentration measurements of any particle species with acoustic contrast with a medium in which it is suspended. The measurement may be used without contact with the fluid being measured.

Furthermore, backscatter spectra which may be generated by embodiments of the invention may provide information about the nature of the particle. For example, differences in the response of the cells with the frequency may imply the existence of more than one type or size of cells. Particle movement or velocities may be generated by Eckart streaming, which is the generation of motion in open volumes of fluid by ultrasound, or simply "streaming". The moving echoes of the particles pushed by this streaming may be used to improve the detection of small echoes from cells within the data processing.

The ultrasound-based device may also comprise a signal generator which creates a signal that is projected into the fluid by the transducer (also called interrogating signal). The signal may for example include a series of pulses or tone bursts, for example, of equal length at the selected central frequency. As indicated above, in a particular embodiment, the signal generator projected by the transducer operates at a central frequency of 20 MHz, and at a pulse of 500 ns, and at a wavelength of 75 μm.

In the period in between pulses, also referred to herein as a "gap", the interrogating signal may be turned off. It is in this interval that the signals may return from the focal zone, e.g., the returning signal may be received during the intervals between the pulses comprising the ultrasonic signal. For example, the focal zone may be about 7 mm from transducer, so the two-way travel distance to the zone and back is 14 mm, and the leading edge of the signal may return to the transducer after 9.3 microseconds (14 mm/1500 m/sec). The returned, backscattered signal may fall between the pulses emitted, where the signal is turned off. The number of the pulses backscattered by cells carries information of the number of cells present at the focal region. The energies of the pulses received depend on the nature of the cells but also on the skin attenuation. Signal processing may separate both effects.

Once the ultrasound data is analyzed by the data processing system, information about cells and/or about their concentration in the fluid is obtained. In a particular embodiment, the cell properties obtained are cell size, cell concentration and/or cell viability.

Finally, in a third step, step c), the first method of the invention comprises correlating the information obtained in step b) with the presence and the amount of circulating cells in the individual, being said circulating cells indicative of the presence of a disease or a pathogenic cell. The correlation between the information obtained in step b) with the presence and the amount of circulating cells may be carried out, for example, by dividing the number of individual ultrasound echoes received by the volume scanned.

In the context of the present invention, a "pathogenic cell" refers to those cells which are in an enough concentration in the human body fluid to trigger an immune response and which are able to cause a disease in the individual.

As the skilled person in the art understands, the information obtained in step b) is in the form of echoes coming from the detected circulating cells. The more circulating cells are in the fluid, the higher amount of echoes is detected. If necessary, there are several ways of improving the cell echo detection in order to obtain a more accurate measurement. Examples of these ways are, without limiting to, increasing the signal amplitude (signal amplitude sweep), measuring the velocity of the cells, and using coded sequences of excitations signals.

Signal amplitude sweep: Tissue attenuation varies locally and also between subjects. High tissue attenuation may prevent from receiving echoes from cells off the focus centre. As a result, true concentration may be underestimated. This effect can be overcome by 2D and 3D scanning where a larger volume is sampled to make sure that enough cells cross the focal volume to have a statistically confident measurement of cell concentration. Alternatively, the maximum energy of the cell echoes received through tissue at the transducer can be related to the maximum energy of cell echoes obtained ex-vivo to estimate the skin attenuation of each patient. This patient-dependent coefficient can be used to correct ex-vivo counts obtained with the method described in Example 1.

Cell velocity: Cell velocity can be induced by either natural fluid flow, the radiation force of the ultrasound signal or the pressure implied by the user on the tissue, which would displace inner structures.

Figure 9:
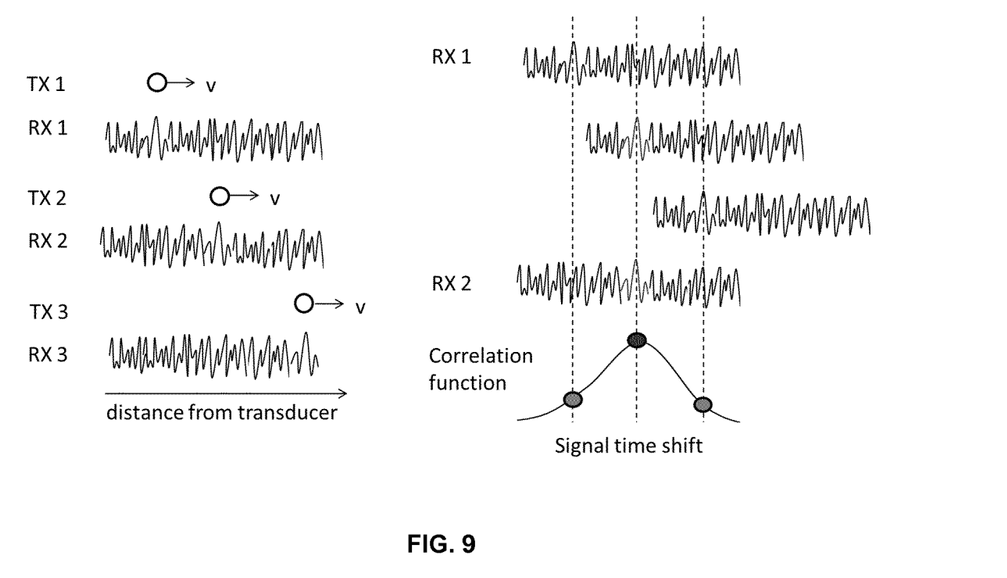
FIG. 9. At each pulse emission, the acoustic pressure exerts a displacement of the particle at a velocity that depends on the energy and repetition frequency of the pulse as well as in the particle and medium properties. The backscatter signal velocity can be tracked, e.g. by correlating consecutive acquisitions (right side of the figure), and used to improve the detection sensitivity of the technique in compromised signal-to-noise conditions.

At low signal to noise ratios (SNRs), single cell velocity increases the detection capabilities of single cell backscatter because it allows differentiating it from noise, which does not propagate. By measuring the velocity of single cells in the suspension, for instance by means of correlation between consecutive data acquisitions, the maximum displacement of the cell for a given time can be known. Hence, the detection capabilities or sensitivity can still be improved by gating or allowing a cell velocity range (as shown in FIG. 9).

Sensitivity improvement by means of coded sequences of excitation signals.

Figure 10:
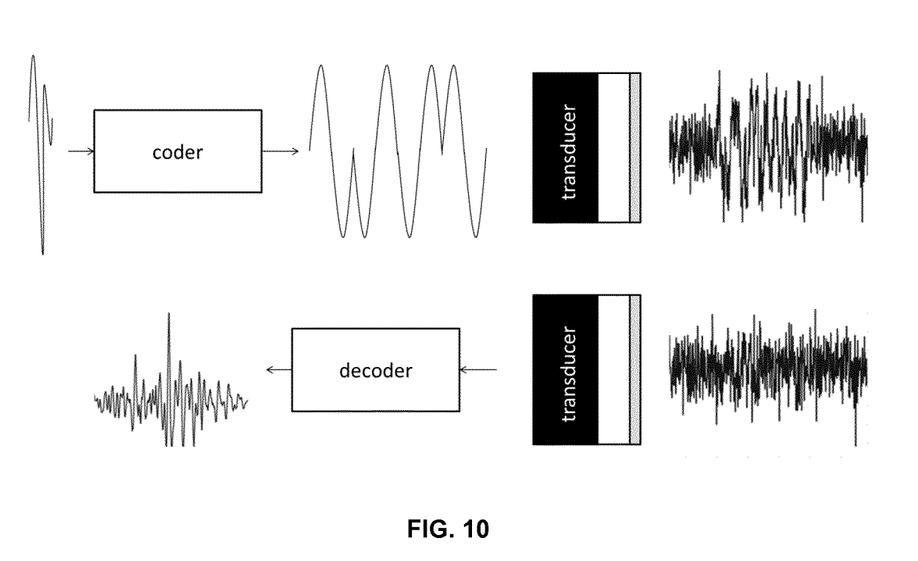
FIG. 10. Schematic of a coding system to enhance cell sensitivity. (Top) In transmission, an electrical impulse is coded to a larger sequence with an overall higher energy. This sequence excites the transducer which converts this energy to a mechanical signal that is input into the system. (Bottom) In receiving mode, the signal may be at SNR close to 0 dB, but the coded pattern can still be recognized (deconvolved, decorrelated) by the decoder, which outputs a peak if the sequence is detected.

In situations when the signal to noise ratio (SNR) is compromised and the power of the signal cannot be increased, e.g. for safety concerns, a coded excitation sequence can be used to increase the SNR. On one hand, the amount of signal energy is larger because instead of a single pulse, multiple pulses are generated. Because the signal is transmitted throughout a longer time, the power is maintained but the spatial resolution is decreased. In order to recover the loss of spatial resolution, the pulse sequence is convolved with a match filter (or coder) that produces a unique signal pattern for the excitation sequence. This is the signal that is sent to the system. In receiving mode, the signal is deconvolved or decoded. For received signals originated from other sources, i.e. noise, the decoder outputs low signal values because the signal pattern is not recognized. Contrarily, when the coded signal is received, the signal is decoded and a high narrow (correlation) peak is produced. Even in simulations with SNR close to zero, this strategy has shown to nicely resolve backscatter from single cells (as shown in FIG. 10).

As explained at the beginning of the present description, the method of the invention is useful as a diagnostic tool, and for monitoring the effectiveness of a treatment administered to a subject suffering from a viral, protozoal, fungal and/or bacterial disease. Therefore, the invention relates to the use of the method of the invention for diagnosing viral, protozoal, fungal and/or bacterial diseases and inflammatory responses to the infection.

Thus, in a second aspect, the invention relates to a method for the diagnosis of a viral, protozoal, fungal and/or bacterial disease in a subject, or for identifying subjects who may be suffering from a viral, protozoal, fungal and/or bacterial disease, hereinafter, second method of the invention, comprising a) quantifying circulating cells in superficial body fluids of the subject by a method according to the first method of the invention, and b) correlating the amount of said circulating cells with the presence of a viral, protozol, fungal and/or bacterial disease in the subject, wherein an amount of circulating cells higher than a reference value is indicative of a viral, protozoal, fungal and/or bacterial disease, or is indicative that the subject may be suffering from a viral, protozoal, fungal and/or bacterial disease.

The reference value is widely known in the state of the art for the different diseases to be diagnosed and is available to the skilled person in order to put the present invention into practice.

As the skilled person in the art understands, all the particular embodiments disclosed for the first method of the invention can be applied to the second method of the invention.

In the context of the present invention, the term "viral disease" refers to a disease caused by a virus, "protozoal disease" refers to a disease caused by protozoa, "fungal disease" refers to a disease caused by a fungus, and "bacterial disease" refers to a disease caused by a bacterium.

The protozoa are single-celled organisms which can be transmitted from one human from another. Those protozoa that have inhabited the human intestine can be transmitted from one human to the other via the fecal-oral route, such as through sharing food the infected person has touched and through direct person to person contact. Protozoa living in the blood can be transmitted through a third source such as a mosquito. There are four main groups of protozoa that cause infection in humans: the sarcodina (ameba), mastigophora (flagellates), ciliophora (ciliates) and the Sporozoa.

Non-limiting examples of protozoan diseases which can be diagnosed with the method of the present invention are amoebiasis (e.g. *Entamoeba histolytica*), giardiasis (e.g. *Giardia lamblia*), african sleeping sickness (e.g. *Trypanosoma brucei*), leishmaniasis (e.g. *Leishmania. major, L. infantum*, and *L. braziliensis*), toxoplasmosis (e.g. *Toxoplasma gondii*), malaria (e.g. *Plamodium falciparum, P. vivax, P. ovale* and *P. malariae*), babesiosis (e.g. *Babesia microti, B. duncani, B. divergens* and *B. venatorum*), trichomoniasis (*Trichomonas vaginalis*).

Fungal diseases are called mycoses and those affecting humans can be divided into groups based on the level of penetration into the body tissues. The subcutaneous mycoses penetrate below the skin to involve the subcutaneous, connective, and bone tissue. The systemic or deep mycoses are able to infect internal organs and become widely disseminated throughout the body. Non-limiting examples of fungal diseases include aspergillosis caused by the fungus *Aspergillus*, cryptococcal infections such as cryptococcal meningitis and cryptococcal pneumonia caused by the fungus *Cryptococcus neoformans* and *C. gattii*, histoplasmosis caused by *Histoplasma capsulatum*, etc.

Examples of bacteria diseases which can be diagnosed by the second method of the invention include meningitis (caused by *Mycobacterium tuberculosis, Neisseria meningitidis, Streptococcus pneumoniae, Haemophilus influenzae* type B, *Listeria monocytogenes* or *Escherichia coli*); encephalitis, pneumonia, tuberculosis, etc.

Examples of viral diseases include, without limiting to, meningitis, chickenpox, flu (influenza), herpes, Human immunodeficiency virus (HIV/AIDS), human papillomavirus (HPV), infectious mononucleosis, mumps, measles, rubella and shingles.

In a particular embodiment, the viral, protozoal, fungal and/or bacterial disease is meningitis.

Thus, the invention relates to a method for the diagnosis of meningitis in a subject, or for identifying subjects who may be suffering from meningitis comprising a) quantifying circulating cells in superficial body fluids of the subject by a method according to the first method of the invention, and b) correlating the amount of said circulating cells with the diagnosis of meningitis, wherein an amount of circulating cells higher than a reference value is indicative of meningitis, or is indicative that the subject may be suffering from meningitis.

The reference value is widely known in the state of the art and, as the skilled person knows, it depends on the age of the patient. Because the blood brain barrier (BBB) becomes less permeable with age, diagnostic levels for Cerebrospinal fluid (CSF) white blood cell (WBC) concentration in meningitis are higher for patients younger than 29 days (>20 WBC/µL) than for patients between 30-90 days (>9 WBC/µL) and than older than 90 days (>5 WBC/µL) (Army, et al. 2003 Am Fam Physician 2003; 68:1103-1108; Edwards et al. 2013. Editor D, Torchia MM. Clinical features and diagnosis of acute bacterial meningitis in children older than one month of age. Up to Date 2013; 1-19).

Additionally, as explained at the beginning of the present description, the present method is especially useful for measuring circulating cells in infants within the CSF without the necessity of performing a lumbar puncture since the measure may be done through the fontanelles. In another particular embodiment, the circulating cells are WBC and/or the superficial body fluid is CSF.

In a third aspect, the invention relates to a method for monitoring the effectiveness of a treatment administered to a subject suffering from a viral, protozoal, fungal and/or bacterial disease, hereinafter, third method of the invention, comprising a) quantifying circulating cells in a superficial body fluid of the subject before and after the treatment by a method according to the first method of the invention, and b) correlating the detection of said circulating cells with the effectiveness of the treatment administered to said subject, wherein an amount of circulating cells in the subject after the treatment lower than the amount of circulating cells before the treatment is indicative that the treatment is being effective.

The terms and expressions used in the third aspect of the invention have been defined and explained previously and can be applied to the present aspect. Likewise, all the particular embodiments relating to previous aspects are also applicable to the third aspect of the invention. As the skilled person in the art understands, it is necessary to leave enough time to the treatment exerts its action over the subject.

Additionally, the presence of circulating cells in the CSF may also be indicative of leukemia. Thus, the invention also relates to a method for the diagnosis of leukemia comprising putting into practice the first method of the invention, and correlating the presence of circulating cells with the presence of leukemia in a subject as explained above for meningitis.

The present invention also encompasses the use embodiments corresponding to the methods of the invention disclosed herein together with the particular embodiments thereof.

Therefore, in another aspect, the invention relates to a non-invasive use of an ultrasound-based device for detecting and quantifying circulating cells in superficial body fluids of a subject, for the diagnosis of viral, protozoal, fungal and/or bacterial disease in a subject, for identifying subjects who may be suffering from a viral, protozoal, fungal and/or bacterial disease, or for monitoring the effectiveness of a treatment administered to a subject suffering from a viral, protozoal, fungal and/or bacterial disease, wherein the ultrasound-based device operates at a central frequency in the range of 10-50 MHz, and at a pulse duration between 50-1,000 ns, and at a wavelength between 30 and 150 µm.

In a particular embodiment, the signal emitted by the ultrasound-based device operates at a central frequency of 20 MHz and/or at a pulse duration of 500 ns, and/or at a wavelength of 75 µm.

In a particular embodiment, the circulating cells are white blood cells, red blood cells or cancer cells.

In a particular embodiment, the superficial body fluid is selected from the group consisting of cerebrospinal fluid, blood, urine, pleural fluid, synovial fluid and pericardial fluid.

In a particular embodiment, the viral, protozoal, fungal and/or bacterial disease is meningitis.

On the other hand, the same measurement principle of the first method of the invention can be applied to an ex-vivo (or in vitro) automatic analysis of liquid samples extracted from the subject. In this case, as a result of the lack of skin attenuation, even higher frequencies could be used, and ultrasound devices may be able to operate between 10-100 MHz with pulses between 25 and 1,000 ns and wavelengths between 15 and 150 µm.

Thus, in a fourth aspect, the invention relates to an in vitro method for detecting and quantifying circulating cells in superficial body fluids of a subject, hereinafter fourth method of the invention, comprising a) placing an ultrasound-based device in contact with a liquid sample isolated from a superficial body fluid of the subject for obtaining an ultrasound data of the liquid sample;

b) analyzing the ultrasound data obtained in step a) by a data processing system which provides information about cells and their concentration in the fluid, and c) correlating the information obtained in step b) with the presence and amount of circulating cells in the individual, wherein the ultrasound-based device operates at a central frequency in the range of 10-100 MHz and at a pulse duration of between 25-1,000 ns, and at wavelengths between 15 and 150 µm.

Again, all the particular embodiments disclosed for the first method of the invention, as well as all the disclosures relating to said embodiments, can be applied to the fourth method of the invention.

Step a) of the third method of the invention comprises placing an ultrasound-based device in contact with a liquid sample isolated from a superficial body fluid of the subject for obtaining an ultrasound data of the liquid sample. As the skilled person in the art understands, the contact between the ultrasound-based device with the liquid sample may be done through the surface of the sample containing recipient. The attenuation of the recipient may be insignificant to the analysis of the ultrasound.

In a fifth aspect, the invention relates to an in vitro method for the diagnosis of a viral, protozoal, fungal and/or bacterial disease in a subject, for identifying subjects who may be suffering from a viral, protozoal, fungal and/or bacterial disease, hereinafter fifth method of the invention, comprising a) quantifying circulating cells in a superficial body fluid of the subject by a method according to the fourth method of the invention, and b) correlating the amount of said circulating cells with the presence of a viral, protozoal, fungal and/or bacterial disease in the subject, wherein an amount of circulating cells higher than a reference value is indicative of a viral, protozoal, fungal and/or bacterial disease, or is indicative that the subject may be suffering from a viral, protozoal, fungal and/or bacterial disease.

In a particular embodiment of the fifth method of the invention, the viral, protozoal, fungal and/or bacterial disease is meningitis.

Finally, in a sixth aspect, the invention relates to an in vitro method for monitoring the effectiveness of a treatment administered to a subject suffering from a viral, protozoal, fungal and/or bacterial disease, hereinafter, sixth method of the invention, comprising a) quantifying circulating cells in a superficial body fluid of the subject before and after the treatment by a method according to the fourth method of the invention, and b) correlating the amount of said circulating cells with the effectiveness of the treatment administered to said subject, wherein an amount of circulating cells in the subject after the treatment lower than the amount of circulating cells before the treatment is indicative that the treatment is being effective.

Again, all the particular embodiments disclosed for the fourth method of the invention, as well as all the disclosures relating to said embodiments, can be applied to the fifth and sixth methods of the invention.

Additionally, the present invention also encompasses the use embodiments corresponding to the methods of the invention disclosed herein together with the particular embodiments thereof.

Therefore, in another aspect, the invention relates to the in vitro use of an ultrasound-based device for detecting and quantifying circulating cells in superficial body fluids of a subject, for the diagnosis of viral, protozoal, fungal and/or bacterial disease in a subject, or for identifying subjects who may be suffering from a viral, protozoal, fungal and/or bacterial disease, or for monitoring the effectiveness of a treatment administered to a subject suffering from a viral, protozoal, fungal and/or bacterial disease, wherein the ultrasound-based device operates at a central frequency in the range of 10-100 MHz and at a pulse duration between 25-1,000 ns, and at a wavelengths between 15 and 150 μm.

In a particular embodiment, the signal emitted by the ultrasound-based device operates at a central frequency of 20 MHz and/or at a pulse duration of 500 ns, and/or at a wavelength of 75 μm.

In a particular embodiment, the circulating cells are white blood cells, red blood cells or cancer cells.

In a particular embodiment, the ultrasound-based device comprises a transducer.

In a particular embodiment, the superficial body fluid is selected from the group consisting of cerebrospinal fluid, blood, urine, pleural fluid, synovial fluid and pericardial fluid.

In a particular embodiment, the viral, protozoal, fungal and/or bacterial disease is meningitis.

Unless otherwise defined, all technical and scientific terms used herein have the same meaning as commonly understood by one of ordinary skill in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples are provided by way of illustration and are not intended to be limiting of the present invention.

BRIEF DESCRIPTION OF THE DRAWINGS

FIG. 6. Diagram showing a single element transducer in contact with a fluid. (Left) The transducer delivers maximum acoustic energy in a focal region. The sensitivity of the transducer is best in the focal region. In order to sample different regions of the liquid, the acoustic beam of the transducer can be mechanically displaced or electronically displaced if multiple elements are used. (Middle) The acoustic pressure exerted into the fluid (or acoustic radiation force) implies a fluid displacement that follows a pattern, i.e. a flow. (Right) If particles are confined in the fluid, they are trapped into the flow as long as their position is within the field of view of the transducer. The higher the energy and pulse repetition frequency, the higher the flow velocity and particles velocity when trapped within the flow.

EXAMPLES

There exists a clinical interest in noninvasively detecting changes in the composition of body fluids. A very clear example is that of the cerebrospinal fluid (CSF), where, currently, only invasive approaches provide accurate information of fluid composition or characteristics. In case of an infection, a major concern is to detect whether an external pathogen has accessed the CSF space. In such case, the immunologic system reacts and sends white blood cells (WBCs) to the site of infection to kill the external organism. In the process of leaving the peripheral blood stream, WBCs penetrate vessel walls and allow blood proteins to leak into the site of infection. The increase of cellularity and protein level in the fluid space progressively changes the bulk properties of the fluid like its density and viscosity.

Example 1

Sample Preparation

CSF mimicking samples were elaborated as an ultrafiltrate version of human blood plasma at varying concentration of white blood cells (WBCs) in the 0-100 cells/μL range. Blood samples from patients with leukocytosis arriving at the fluid analysis laboratory in the hospital were collected in tubes and treated with disodium ethylenediaminetetraacetate (EDTA). The tubes were centrifuged at 300 g for 10 minutes and 1-2 mL of plasma from each EDTA tube was used to create a pool of plasma. Pool proteins were measured and saline serum was added to obtain a final plasma volume of 50 mL at 0.5 g/L proteins level. This protein matrix constituted our healthy mock CSF. From each EDTA tube, 1 mL of buffy coat was pipetted out with a Pasteur pipette and transferred to a Wintrobe tube. The ten Wintrobe tubes were then centrifuged at 300 g for 10 minutes. For each tube, the WBC layer was pipetted out and diluted in 1-mL of the protein matrix. From this 1 mL stock suspension, cell dilutions were prepared to obtain concentrations in the range 0-100 WBC/μL. Cell count and differential was performed by means of a Fuchs Rosenthal hemocytometer.

Methods

Figure 1:
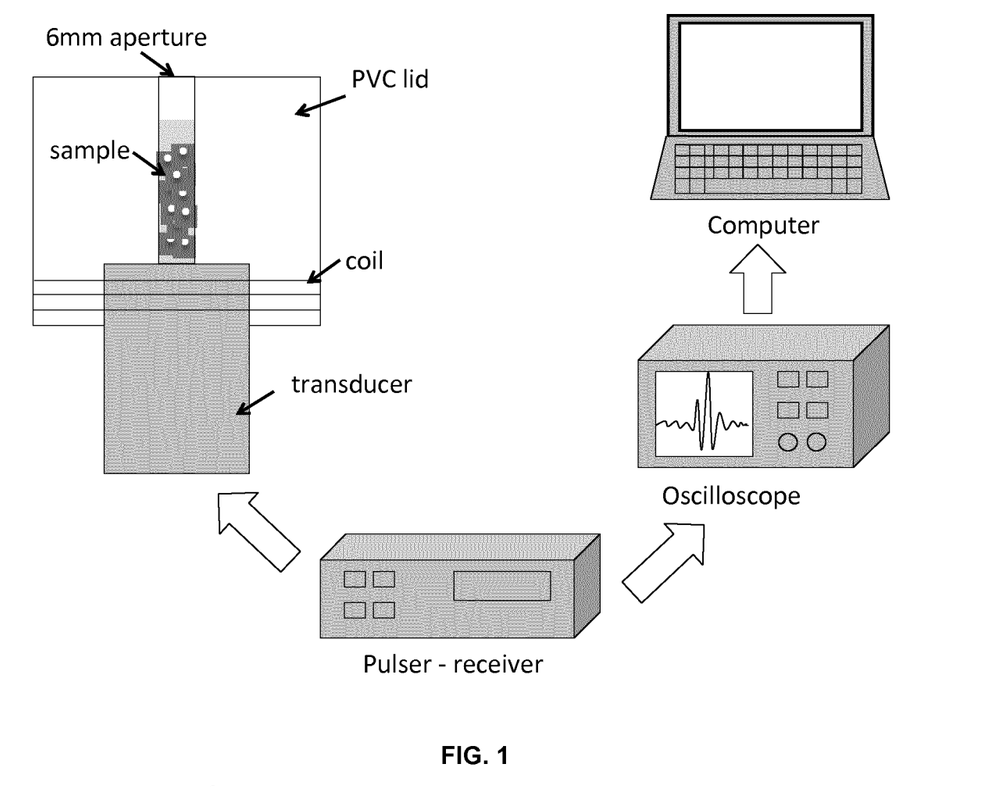
FIG. 1. Schematic diagram of the method used.

Cell samples were ultrasonically scanned using a single element transducer (V3320, Olympus, Waltham, Mass., USA). The transducer centre frequency was 75 MHz with a −6 dB bandwidth ranging from 42.5 MHz to 101 MHz, a focus located at 12.5 mm and an f-number of 2. The transducer was excited with a Panametrics 5900PR pulser (Olympus, Waltham, Mass., USA) and connected to a Picoscope 6402D oscilloscope (Pico Technology, Cambridgeshire, United Kingdom). Sequential RF signals centred in the focus were acquired and stored in a workstation for post-processing. Cell samples were put in direct contact with the transducer and contained in a specifically designed PVC lid that was coiled onto the transducer. As a result of the attenuation through the liquid medium and the cell response, the pulse received is centered at 45 MHz, having a wavelength of 33 μm and 45 ns pulse duration. Samples were pipetted in and out of the lid cavity through a 6 mm aperture (FIG. 1). Samples were kept at 4° C. and measured within three hours from sample elaboration to maintain cell viability levels above 90%. A 450 μL sample volume was used to guarantee immersion of the acoustic focus in the sample. The backscatter coefficient was computed from the RF signals using the method described in FIG. 1 and compared to the hemocytometer results. The time and frequency response of the backscattered signal coming from cells was theoretically studied using Anderson's model with a Poisson modulus close to 0.5, the value used for cells in this frequency range.

Results

Figure 2:
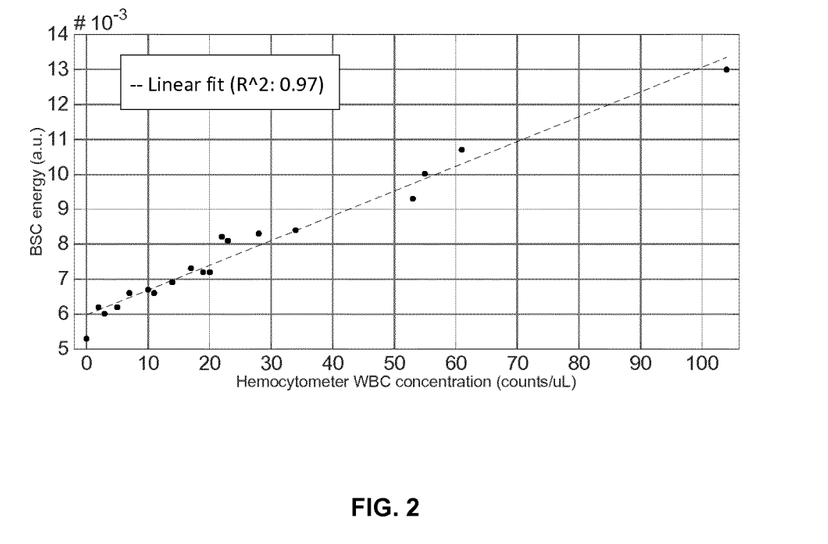
FIG. 2. Ultrasound backscatter coefficient in relation to the WBC concentration measured with a Fuchs Rosenthal hemocytometer. The dashed lines represents the linear fit that explains the backscatter variability of the data when compared to WBC concentration (97%), as measured by means of the coefficient of determination, $R^2$. This figure shows the capabilities of high-frequency ultrasounds to confidently distinguish WBC concentrations below and above the meningitis diagnostic threshold of 10 cells/μL and 20 cells/μL set for 1-3 months old infants and neonates, respectively. For in vivo validation, the system needs to be adjusted to counteract the fontanelle attenuation to maintain diagnostic sensitivity.

FIG. 2 shows two linear trends that put in relation the backscatter energy to the total WBC counts and to the WBC counts as measured with the hemocytometer. Results showed linear agreement of the backscatter signal with increasing WBC ($R^2$: 0.97).

Example 2

Cell Sample Preparation
See example 1 above.

Methods

Cell samples were ultrasonically scanned using a commercial ultrasound system (DermaScan C USB, Corex Technologies, Hadsund, Denmark). The transducer centre frequency was 20 MHz (pulse wavelength, 75 μm) with a −6 dB bandwidth ranging from 17.5 MHz to 22.5 MHz, a system resolution of 60 μm (axial)×150 μm (lateral), a focus located at 6 mm, a linear scan of 1.21 mm and a frame-rate of 5 fps.

Figure 3:
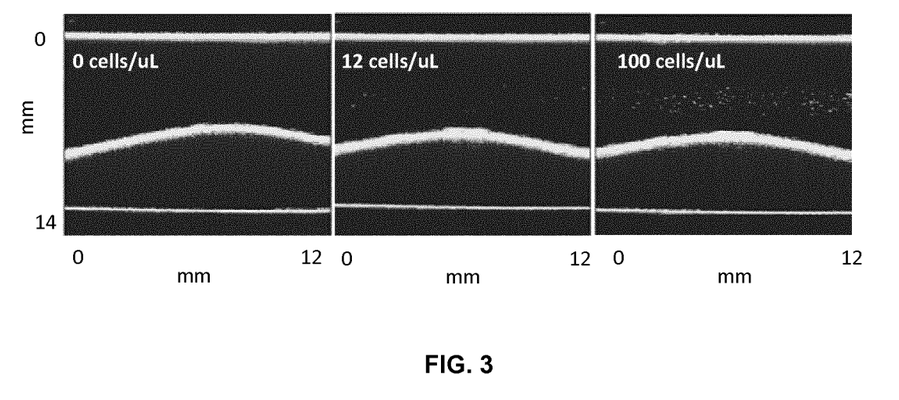
FIG. 3. 2D ultrasound image of CSF samples at WBC concentrations 0, 12 and 100 cells/μL as measured with hemocytometer. An increased number of scatterers (cells) are observed in the image with increased WBC concentration. No scatterer (cell) is observed at 0 cells/μL and that individual scatters can be observed up to 100 cells/μL.

Results 2D images were obtained from the imaging system for concentrations from 0-100 cells/μL. FIG. 3 shows three images corresponding to 0, 12 and 100 WBC/μL samples. Individual echoes observed in the images may be attached to single cells despite of the system resolution-to-particle size mismatch. In the long wavelength limit where the wavelength of the acoustical energy being scattered may be greater than the size of a weakly scattering (nonresonant) particle, i.e., $\lambda > 2\pi a$ where $\lambda$ may represent the wavelength and "a" may represent the particle radius, the backscattered energy may be due to Rayleigh scattering and it may depend on the contrast between the compressibility and density of the particle and that of the fluid suspension medium, and the volume of the particle. The axial resolution given by the manufacturer is 60 μm and the radii of the WBC in the sample were of about 6 μm. As a result, $2\pi a/\lambda$ equals 0.63 (<1 with $a/\lambda < 1/10$) concluding that the backscattering effect is within the Rayleigh regime.

Example 3

Non-Invasive Diagnosis of Meningitis

Bacterial Meningitis (BM) is a very aggressive disease that affects the central nervous system and that still causes high morbidity and mortality among young infants and neonates. In developing countries mortality is about 40-58% and about 10% in developed countries. The clinical presentation of this disease is very specific being fever the most common and sometimes only symptom. Diagnosis requires a sample of the cerebrospinal fluid (CSF), a fluid that surrounds the brain and spinal cord. Currently, the lumbar puncture is the only way to obtain a sample of the CSF to analyze its composition characteristics. However, the lumbar puncture is an invasive procedure, difficult to perform in the infants and neonates and very often (up to 48%) traumatic, meaning that blood contaminates the sample leading to unreliable CSF results. In developing countries where the incidence of the disease is 10 (in endemic regions) or even 100 times (in epidemic seasons) than in developed countries (10 cases per 100.000 people), it is common that a lumbar puncture is never performed because of the lack of laboratory facilities to analyze the sample. Hence, diagnosis is heavily based on the clinical symptomatology perceived by the physician or in his/her absence the nurse, who follows a clinical protocol. In developed countries, where laboratory facilities are abundant and given the poor prognosis for an infected patient in case of delayed treatment, physicians have a low threshold to perform a lumbar puncture in patients with meningeal symptoms (e.g. fever). Moreover, patients with an increased CSF WBC count (over 20 cells/μL in newborns <1 month, and over 10 cells/μL in infants 1-3 months old) will immediately get empirical antibiotic treatment for BM until the CSF bacterial culture result is available (after 48-72 hours). Although a safe strategy, this results in up to 95% of infants without BM receiving a lumbar puncture and many of them also treated with antibiotics. Therefore, in developed countries—where the incidence of BM is low—this strategy does not add any benefit to the non-BM patients's healthcare. So for under-resourced as developed countries we think that better and easy-to-use methods are needed.

Figure 4:
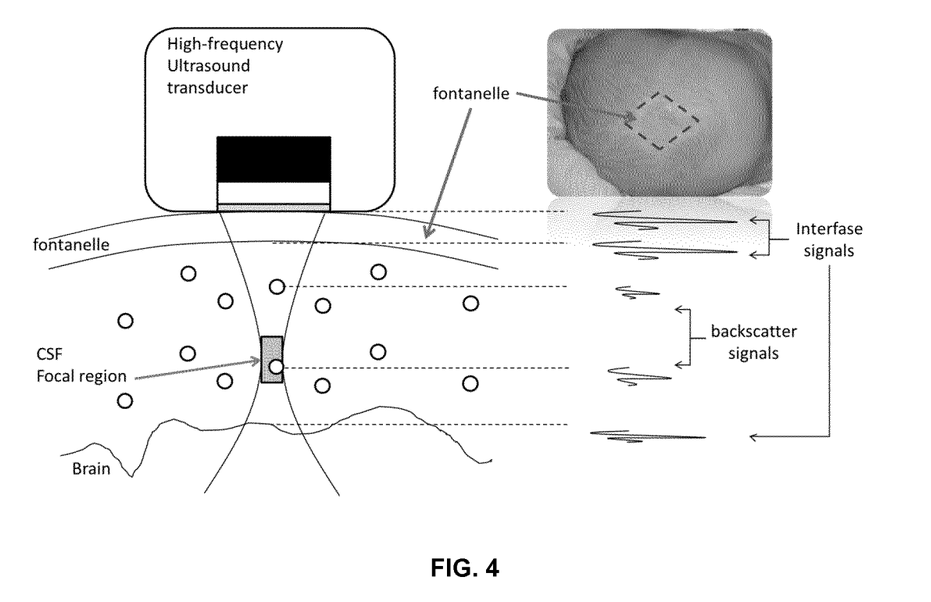
FIG. 4. Diagrammatic description of cells detection in the CSF space. A first group of signals is reflected from the fontanelle layers, a second group of backscatters is obtained if cells are present in the fluid and, a third group of signals are reflected from the fluid-brain interface. This last group of signals can be used to indicate optimal alignment of the transducer, as it is orthogonal to all tissue layers.

The method of the invention uses high-frequency ultrasounds to sense the presence of cells in the CSF through the fontanelle (FIG. 4) and signal processing to detect individual cells and provide CSF cell concentration to assist in the non-invasive diagnosis of meningitis as well as reducing the number of lumbar punctures to those that are only strictly necessary.

High frequency ultrasound manufacturers:
Pre-Clinical Imaging
VisualSonics Inc. (Canada)
Atys medical (France)
Dermatology
Atys medical (France)
TPM, Taberna Pro Medicum (Germany)
Cortex technologies (Denmark)
Sonoscape (China)
Sonosite, Inc (USA)
Longwood, Inc (USA)
Esaote (Italy)
GE Healthcare (US)

Figure 5:
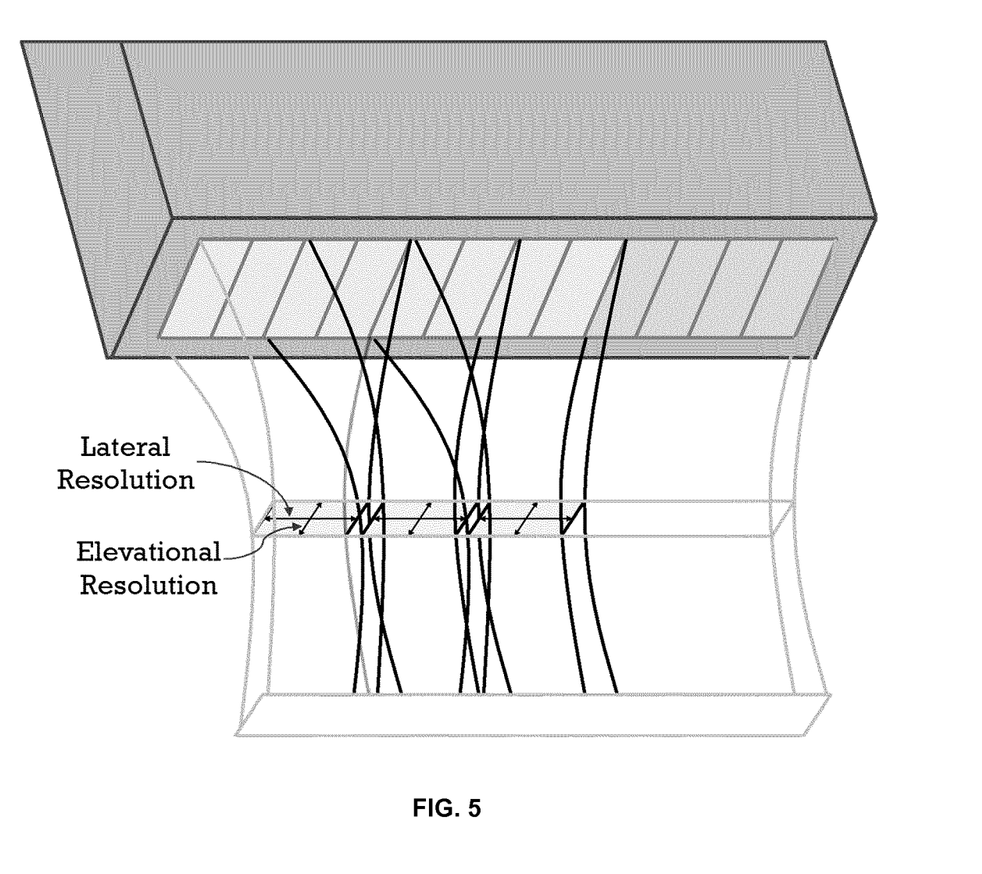
FIG. 5 shows a transducer array which can be used to focalize the ultrasound energy at different points.

1. Acustic Fundamental and Concept Development
1.1 Sampling
1.1.1. Volume Sampling The ultrasound device (or transducer) applies a pressure signal that is maximum in a small region, i.e. the focal region, of the liquid volume. If the device is comprised by one single element that remains static, only one-dimensional data is obtained. If multiple regions of the fluid volume are going to be sampled, the single element can be mechanically or electronically displaced and two- or three-dimensional data (or images) can be obtained. When using multiple elements, an acoustic beam can be electronically steered to image a portion or the entire liquid volume (FIG. 5).

1.1.2 Focused Acoustic Radiation Force

Figure 6:
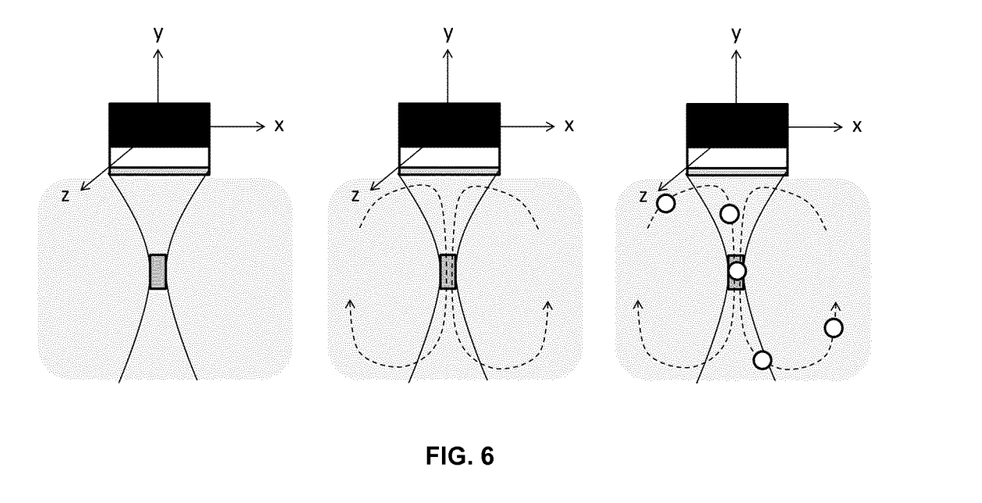

The acoustic pressure applied by the transducer generates an acoustic radiation force that may induce a flow in the liquid volume. Such flow increases as the pulse repetition frequency (PRF) also increases, i.e. the frequency at which the pressure signal is emitted, and is maximum in the focal region (FIG. 6).

1.2 Fluid Characterization
1.2.1 Acoustic Backscatter of Single Cells

Figure 7:
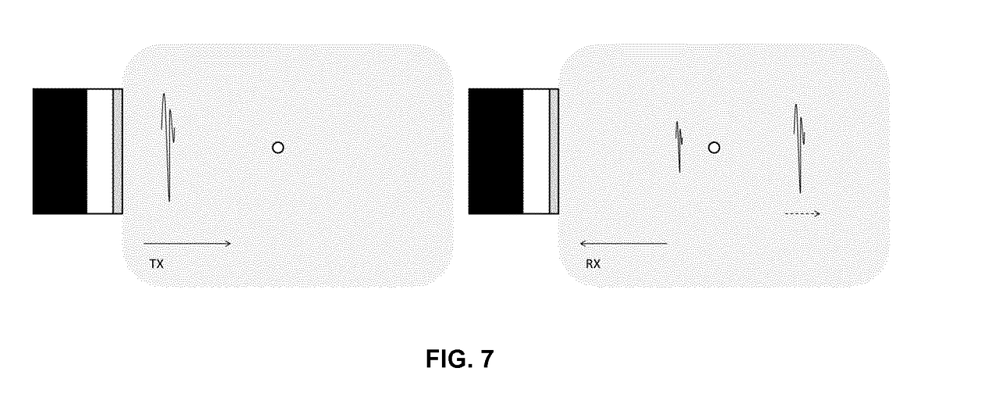
FIG. 7. Backscatter signal of a particle is that signal reflected back to the transducer by a scattering object. The closer the wavelength of the emitted signal is to the scatter diameter, the higher the backscattered signal. As observed in the right diagram, the emitted signal keeps propagating in the fluid at with a lower energy since part of the energy is reflected by the particle and part is being attenuated by the medium.

If there are cells in the liquid volume (a suspension), part of the pressure signal is reflected by the cells back to the transducer (FIG. 7). These reflected signals from single cells are called acoustic backscattered signals or backscatter. Backscatter energy increases as the wavelength of the emitted signal approaches the size of the cell, i.e. the frequency of the emitted signal increases. Therefore, whenever we refer to the transducer in the text, it should be understood that we are referring to a high-frequency transducer. Signal and data processing is also needed to provide a measurement of cell concentration (see section 2).

1.2.2 Spectral Content of Backscatter from Cells

Figure 8:
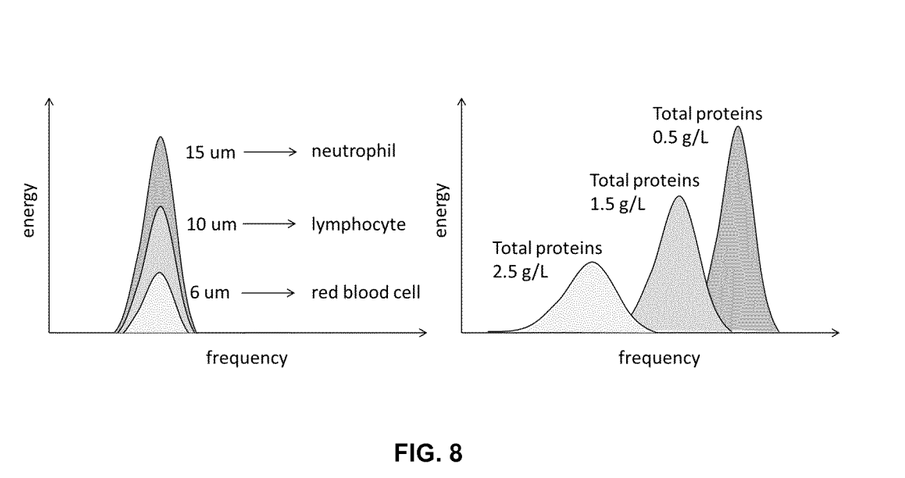
FIG. 8. (Left) Backscatter spectra of cells of different size show an increase energy as the cell diameter increases. In a larger band implementation (ex-vivo application) the maximum of the frequency will be also be displaced towards higher frequencies for smaller cells. (Right) Backscatter spectra is shifted to lower frequencies and widens in bandwidth as the attenuation of the medium is increased by higher protein concentrations.

The spectral content of a backscatter signal is a hallmark of the cell producing such backscatter signal. Cell properties like size and composition are related to the energy, frequency and bandwidth of the backscatter signal. Similarly, the viscosity of the suspension medium can also be related to frequency shifts and bandwidth changes of the backscatter spectrum as well as from the spectrum of the signal reflected at the interface between the fluid and the distal wall of the container. Such analysis is only possible at very low skin attenuation or ex-vivo liquid analysis (FIG. 8).

1.2.3 Cell Velocity

Cell velocity can be induced by either natural fluid flow, the radiation force of the ultrasound signal or the pressure implied by the user on the tissue, which would displace inner structures.

At low SNRs, single cell velocity increases the detection capabilities of single cell backscatter because it allows differentiating it from noise, which does not propagate. By measuring the velocity of single cells in the suspension, for instance by means of correlation between consecutive data acquisitions, the maximum displacement of the cell for a given time can be known. Hence, the detection capabilities or sensitivity can still be improved by gating or allowing a cell velocity range (FIG. 9).

1.2.4 Sensitivity Improvement by Means of Coded Sequences of Excitation Signals

In situations when the SNR is compromised and the power of the signal cannot be increased, e.g. for safety concerns, a coded excitation sequence can be used to increase the SNR. On one hand, the amount of signal energy is larger because instead of a single pulse, multiple pulses are generated. Because the signal is transmitted throughout a longer time, the power is maintained but the spatial resolution is decreased. In order to recover the loss of spatial resolution, the pulse sequence is convolved with a match filter (or coder) that produces a unique signal pattern for the excitation sequence. This is the signal that is sent to the system. In receiving mode, the signal is deconvolved or decoded. For received signals originated from other sources, i.e. noise, the decoder outputs low signal values because the signal pattern is not recognized. Contrarily, when the coded signal is received, the signal is decoded and a high narrow (correlation) peak is produced. Even in simulations with SNR close to 0, this strategy has shown to nicely resolve backscatter from single cells (FIG. 10).

1.3 Structural Measurements
1.3.1 Liquid Thickness Calculation

When the body fluid is confined between two tissues, the thickness of the fluid can be estimated based on the sound speed of the signal in the fluid and the time distance of the reflected signals at the interfaces of the tissues surrounding the fluid.

The signal received by the transducer should be composed by a first set of reflections from the outer tissue, a second signal representative of the content in the fluid (backscatters of cells, if any), and a last set of reflected signals from the shallowest tissue surrounding the fluid.

1.4. Operational Factors
1.4.1. Alignment Check

Continuing with the above description, when this received signal structure and organization is not given, this means that at least one of the tissue components is not in the field of view of the transducer. By repositioning or reorienting the transducer, the sets of reflected signals can be recognized, which would indicate that the alignment of the transducer is correct. At this point, single-cell backscatter signals coming from the fluid can be isolated or gated and further analyzed. Note the fact of not receiving a reflection from the deeper tissue surrounding the fluid does not necessarily prevent from receiving single-cell backscatters from the fluid.

2. Signal Processing and Analysis
2.1 Backscatter Energy Analysis in a Frequency Range of Interest The returned backscattered signal is time-gated to include only the acoustic focus, which is located at a distance between 5-15 mm and has a length ranging from the hundreds of micrometers up to 2 mm. The focal volume is the region with a maximum sensitivity to cells in the fluid. The signal is Fast Fourier transformed and the power spectrum in the 15-30 MHz frequency range is analysed to calculate cell concentration and cell properties.

2.2 Improved Cell Echo Detection 2.2.1 Cross-Correlation

Consecutive RF signals (or its enveloped version) are cross-correlated to find signal linear coherence due to cells. After normalization of the cross-correlation signal to the energy of the RF signals, a threshold ranging from 0.3-0.9 is used to identify cross-correlation peaks that can be attached to the echoes from cells. At acquisition rates in the order of tenths of milliseconds, the shift of cross-correlation peaks corresponding to a moving cell through the focus is used to determine cell velocity. Alternatively, the phase shift of the spectral backscatter frequency peak can be used. If a 2D-3D image is obtained by means of a linearly scanned single element transducer or a linear array or a 2D array, the Hough transform can be applied to the data as an efficient technique to detect cells, their trajectory and speed. Hough-transformed data might be later thresholded before a cell detection algorithm is used to count the number of cells.

2.2.2 Coded Excitation

Coded excitation techniques (chirp, golay, barker) are used to improve the signal-to-noise ratio of the received backscatter signal. A pulse is coded by a match filter into a sequence or combination of sequences and transmitted into the body. The received signal is then deconvoluted by a duplicate of the matched filter in the receiver circuit producing a distinct spectral peak in the pulse frequency band only if the received signal signature matches the coded sequence of the match filter.

2.3 Volume Estimation 2.3.1 Cell Echo Intensity-Based Method (1D or 2D)

An estimation of the sampled volume can be obtained by putting into relation the average intensity level of cell echoes in the focal region with respect to an effective focal volume previously measured at different attenuations because the larger the attenuation the more reduced the effective sampled volume. To this aim, the intensity frequency distribution of cell echoes is binned and distribution parameters such as intensity levels span over a probability threshold, e.g. 10%, are calculated. The larger the cell echoes intensity levels span the larger the focal volume that is being sampled. This relationship between intensity levels span and effective sampled volume can be calibrated for different attenuations. Alternatively, the intensity levels shift can be mapped to the effective sampled volume. The lower the cell echoes intensity levels the larger the attenuation and the smaller the effective sampled volume. Similarly, the intensity shift of cell echoes in relation to the effective sampled volume can be previously calibrated.

2.3.2 2D Array, Linearly Scanned 1D Array, 2D-Scanned Single Element

If a 3D volume is obtained by means of a 2D array, a linearly scanned linear array or a 2D-scanned single element, the volume can be estimated with minimal error from the image voxel dimensions.

2.4 Cell Properties and Viability

Cell concentration, size and viability can be determined from the spectral energy, the spectral bandwidth or the spectral slope of the returned cell backscattering signal.

Cell backscatter energy is linearly related to cell concentration in the range 0-100 cells/µL. At higher concentrations the cell backscatter is attenuated by cells located between the scattering cell and the transducer in the direction of the backscatter signal.

Size is determined by cell echo width if a 3D image is obtained by relating the echo intensity with the size of the cell.

Cell viability can be determined by combination of backscatter energy (measure of cell nucleus hardness) and spectral slope (measure of scatterer's size) in the frequency range of interest. There are different ways of cell death involving different structural changes of the nucleus. In apoptosis, the nucleus is condensed and fragmented reducing the size of the cell, increasing the backscattered energy, and preserving the spectral slope. In mitotic arrest/catastrophe the cell and nucleus size increase, the backscatter energy increases but the spectral slope decreases.

The invention claimed is:

1. An in vitro method for detecting and quantifying circulating cells in superficial body fluids of a subject comprising
   a) placing an ultrasound-based device in contact with a liquid sample isolated from a superficial body fluid of the subject for obtaining a ultrasound data of said liquid sample;
   b) analyzing the ultrasound data obtained in step a) by a data processing system which provides information about cells and their concentration in the fluid, and
   c) correlating the information obtained in step b) with the presence and amount of circulating cells in the individual,
   wherein the ultrasound-based device operates at a central frequency in the range of 10-100 MHz and at a pulse duration between 25-1,000 ns, and at a wavelengths between 15 and 150 µm.

2. The method according to claim 1, wherein the signal emitted by the ultrasound-based device operates at a central frequency of 20 MHz and/or at a pulse duration of 500 ns, and/or at a wavelength of 75 µm.

3. The method according to claim 1, wherein the circulating cells are white blood cells, red blood cells or cancer cells.

4. The method according to claim 1, wherein the ultrasound-based device comprises a transducer.

5. The method according to claim 1, wherein the ultrasound data obtained in step a) is in the form of (i) collection of A-line data and/or of (ii) B-mode or C-mode type of 2D data or 3D data.

6. The method according to claim 1, wherein the information about cells is cell size, cell concentration and/or cell viability.

7. The method according to claim 1, wherein the superficial body fluid is selected from the group consisting of cerebrospinal fluid, blood, urine, pleural fluid, synovial fluid and pericardial fluid.

8. An in vitro method for the diagnosis of a viral, protozoal, fungal and/or bacterial disease in a subject or for identifying subjects who may be suffering from a viral, protozoal, fungal and/or bacterial disease comprising
   a) quantifying circulating cells in superficial body fluids of the subject by a method according to claim 1, and
   b) correlating the amount of said circulating cells with the presence of a viral, protozoal, fungal and/or bacterial disease in the subject, wherein an amount of circulating cells higher than a reference value is indicative of a viral, protozoal, fungal and/or bacterial disease, or is indicative that the subject may be suffering from a viral, protozoal, fungal and/or bacterial disease.

9. An in vitro method for monitoring the effectiveness of a treatment administered to a subject suffering from a viral, protozoal, fungal and/or bacterial disease, comprising
   a) quantifying circulating cells in a superficial body fluid of the subject before and after the treatment by a method according to claim 1, and
   b) correlating the amount of said circulating cells with the effectiveness of the treatment administered to said subject,
   wherein an amount of circulating cells in the subject after the treatment lower than the amount of circulating cells before the treatment is indicative that the treatment is being effective.

10. An in vitro method according to claim 8, wherein the viral, protozoal, fungal and/or bacterial disease is meningitis.

11. A non-invasive method for detecting and quantifying circulating cells in superficial body fluids comprising
   a) placing an ultrasound-based device on the skin of the subject for obtaining a ultrasound data of the a superficial body fluid under the skin;
   b) analyzing the ultrasound data obtained in step a) by a data processing system which provides information about cells and their concentration in the fluid, and
   c) correlating the information obtained in step b) with the presence and amount of circulating cells in the subject,
   wherein the ultrasound-based device operates at a central frequency in the range of 10-50 MHz, and at a pulse duration between 50-1,000 ns, and at a wavelength between 30 and 150 μm.

12. The method according to claim 11, wherein the signal emitted by the ultrasound-based device operates at a central frequency of 20 MHz and/or at a pulse duration of 500 ns, and/or at a wavelength of 75 μm.

13. The method according to claim 11, wherein the circulating cells are white blood cells, red blood cells or cancer cells.

14. The method according to claim 11, wherein the ultrasound-based device comprises a transducer.

15. The method according to claim 11, wherein the ultrasound data obtained in step a) is in the form of (i) collection of A-line data and/or of (ii) B-mode or C-mode type of 2D data or 3D data.

16. The method according to claim 11, wherein the information about cells is cell size, cell concentration and/or cell viability.

17. The method according to claim 11, wherein the superficial body fluid is selected from the group consisting of cerebrospinal fluid, blood, urine, pleural fluid, synovial fluid and pericardial fluid.

18. A method for the diagnosis of a viral, protozoal, fungal and/or bacterial disease in a subject or for identifying subjects who may be suffering from a viral, protozoal, fungal and/or bacterial disease, comprising
   a) quantifying circulating cells in superficial body fluids of the subject by a method according to claim 11, and
   b) correlating the amount of said circulating cells with the presence of a viral, protozoal, fungal and/or bacterial disease in the subject, wherein an amount of circulating cells higher than a reference value is indicative of a viral, protozoal, fungal and/or bacterial disease, is indicative that the subject may be suffering from a viral, protozoal, fungal and/or bacterial disease.

19. Method for monitoring the effectiveness of a treatment administered to a subject suffering from a viral, protozoal, fungal and/or bacterial disease comprising
   a) quantifying circulating cells in a superficial body fluid of the subject before and after the treatment by a method according to claim 11, and
   b) correlating the detection of said circulating cells with the effectiveness of the treatment administered to said subject,
   wherein an amount of circulating cells in the subject after the treatment lower than the amount of circulating cells before the treatment is indicative that the treatment is being effective.

20. Method according to claim 18, wherein the viral, protozoal, fungal and/or bacterial disease is meningitis.

* * * * *